United States Patent [19]

Lee

[11] Patent Number: 4,840,624
[45] Date of Patent: Jun. 20, 1989

[54] FEMALE CONDOM DEVICE

[76] Inventor: Henry J. Lee, 2521 Harriman Cir., Tallahassee, Fla. 32312

[21] Appl. No.: 100,426

[22] Filed: Sep. 24, 1982

[51] Int. Cl.⁴ ............................................. A61F 5/44
[52] U.S. Cl. .................................... 604/349; 604/353
[58] Field of Search .............. 604/353, 351, 327, 328, 604/330–335, 349, 350, 348, 347

[56] References Cited

U.S. PATENT DOCUMENTS

| | | | |
|---|---|---|---|
| 1,866,060 | 7/1932 | Schmidt | 604/353 |
| 2,348,773 | 5/1944 | Wyman | 604/349 |
| 2,591,783 | 4/1952 | Craddock | 604/353 |
| 2,839,061 | 6/1958 | Inscho | 604/347 |
| 3,194,238 | 7/1965 | Breece, Jr. | 604/329 |
| 3,353,538 | 11/1967 | Carrigan | 604/353 |
| 3,528,423 | 9/1970 | Lee | 604/329 |
| 4,182,332 | 1/1980 | Delaney | 604/328 |
| 4,615,692 | 10/1986 | Giacalone et al. | 604/330 |
| 4,664,104 | 5/1987 | Jaicks | 604/353 |
| 4,692,160 | 9/1987 | Nussbaumer | 604/331 |

FOREIGN PATENT DOCUMENTS

| | | | |
|---|---|---|---|
| 1158507 | 12/1983 | Canada | 604/349 |
| 0214764 | 10/1984 | German Democratic Rep. | 604/353 |
| 117234 | 10/1926 | Switzerland | 604/349 |
| 25729 | of 1899 | United Kingdom | 604/347 |

Primary Examiner—James C. Yeung

[57] ABSTRACT

Female condom device having a pubic area cover pad with a condom attached perpendicularly thereto with its open end in the middle of the pad and the closed end extending rearwardly from the pad; leg encircling tapes for holding the pad in place, and, optionally, an insertion tool having an elongated cylindrical body adapted to insert the condom portion into the vagina of the wearer.

3 Claims, 1 Drawing Sheet

FEMALE CONDOM DEVICE

BACKGROUND OF THE INVENTION

Among the contraceptive devices of the past has been the condom worn by the male over the penis to catch his sperm and prevent it from passing into the uterus of the female. Female contraceptive devices have included barriers such as a diaphragm or intrauterine ring which are inserted into the uterus or vagina to prevent passage of sperm. The present concern over diseases, such as AIDS, has focused attention on contraceptives, such as condoms, which prevent actual contact between the male and female genitalia during intercourse.

It is an object of this invention to provide a female condom device. It is another object of this invention to provide a device adapted to be worn by the female to prevent physical contact between the male and female genitalia during intercourse. Still other objects will become apparent from the more detailed description which follows.

BRIEF SUMMARY OF THE INVENTION

This invention relates to a female condom device comprising a soft triangular public area cover pad having a front side and a back side, a thin tubular condom portion having an open end and a closed end, affixed to said pad with said open end generally in the center of said front side and said closed end extending outwardly from said back side, and hip engaging elongated tapes extending outwardly from the three corners of said pad.

In specific embodiments of this invention the device includes elastic tapes to fit around the legs of the wearer, and preferably also a waist belt attached to the leg tapes. Preferably the device includes an insertion tool for insering the condom portion into the vagina.

BRIEF DESCRIPTION OF THE DRAWINGS

The novel features believed to be characteristic of this invention are set forth with particularlity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The female condom device of this invention is best understood by reference to the attached drawings.

Figure 1:
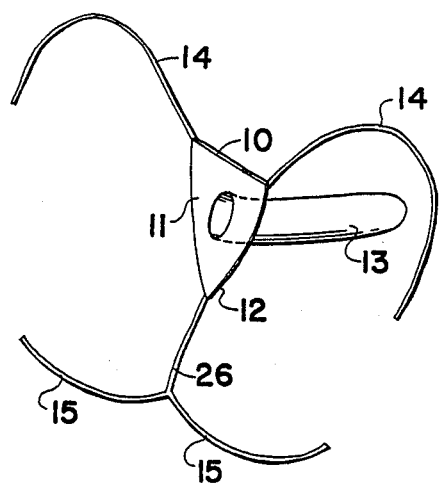
FIG. 1 is a perspective view of one embodiment of the device of the invention.
Figure 2:
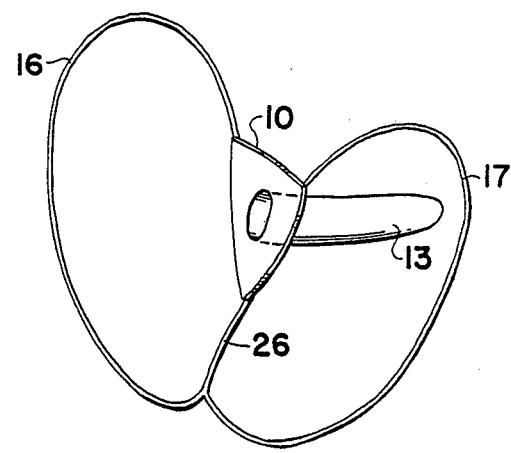
FIG. 2 is a perspective view of a second embodiment of the device of the invention.
Figure 3:
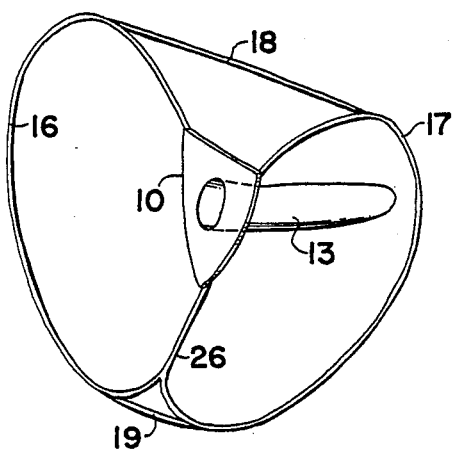
FIG. 3 is a perspective view of a third embodiment of the device of the invention.
Figure 4:
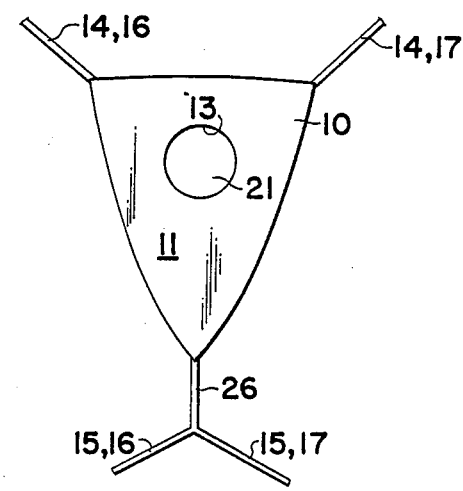
FIG. 4 is a side elevational view of the device of the invention.
Figure 5:
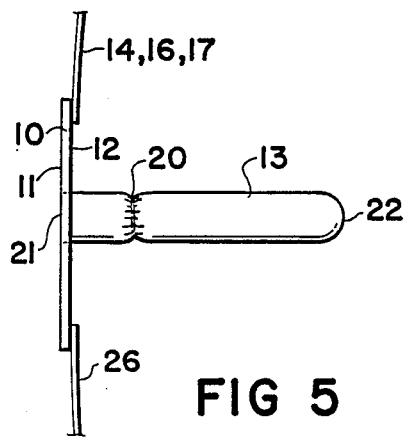
FIG. 5 is a front plan view of the device of the invention.
Figure 6:
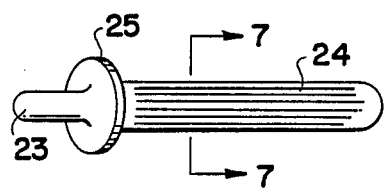
FIG. 6 is a perspective view of the insertion tool of the invention.

In FIGS. 1-3 there are shown three embodiments of the invention which differ from each other only in the types of leg tapes and waist belts employed. The central portion of the device is shown in FIGS. 4-5 and this portion is unchanged in the embodiments of FIGS. 1-3. FIG. 6 shows an optional tool employed in positioning the device on a female body.

The female condom device of this invention includes a triangular public area cover pad 10 having a front side 11 and a back side 12. Attached to pad 10 is a condom 13 which passes through pad 10 in a position generally perpendicular to pad 10. The open end 21 of condom 13 is on front side 11 of pad 10 and the remainder of condom 13 to and including closed end 22 extends outwardly from back side 12 of pad 10. Pad 10 may be any soft material such as cotton, wool, or synthetic fiber fabric, plastic sheeting, foamed plastic, foamed rubber, or the like. Preferably pad 10 is impervious to moisture and is made of a foamed plastic covered with a soft cotton fabric. Condom 13 is a thin flexible sheath substantially identical to male condoms sold commercially today, and especially those having an elastically expandible constricted encircling zone 20 spaced apart from, buy adjacent to, back side 12 of pad 10. Such a constriction zone helps to keep condom 13 attached to the male penis.

The central portion including pad 10 and condom portion 13 is held on the female body by leg encircling tapes attached to the three corners of pad 10 as shown in FIGS. 1-3. In FIG. 1 tapes 14 are attached to the upper corners of pad 10 and tapes 15 are both attached to a single extension tape 26 fastened to the lower corner of pad 10. Each of tapes 14 and 15 have free ends which can then be tied together to form two leg encircling loops. In FIG. 2 tape 16 forms one loop (for the right leg) and tape 17 forms a second loop (for the left leg). In this instance tapes 16 and 17 should be elastic to form a snug fit around each leg. In FIG. 3 the two elastic loops 16 and 17 are joined to each other by one or both of waist belts 18 and 19. Belt 18 extends across the abdomen of the wearer and belt 19 extends across the back of the wearer.

Figure 7:
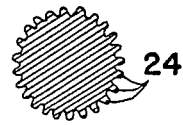
FIG. 7 is a cross section taken at 7—7 of FIG. 6.

For assistance in positioning condom portion 13 inside the vagina of the wearer there is provided the insertion device of FIGS. 6-7. Shaft portion 24 is inserted inside condom portion 13 and manipulated by handle 23 to push condom portion 13 into the vagina, and the insertion device is then removed. A guard flange 25 may optionally be included to provide an insertion depth gauge. Preferably the outside surface of shaft portion 24 is corrugated with longitudinal ribs 27 to permit air to flow outwardly along ribs 27 as the shaft portion 24 is inserted into condom portion 13.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A female condom device comprising a triangular pubic area cover pad having a front side and a back side, a thin elastomeric tubular condom portion affixed to said pad with the opening of said condom portion generally in the center of said front side and the closed end of said condom extending outwardly from said back side, and two hip engaging elongated loops of tape extending outwardly from the three corners of said pad;

said condom portion having an expandible constricting encirclement spaced rearwardly from and adjacent to said cover pad.

2. The female condom device of claim 1 wherein said cover pad is a foamed plastic sheet covered with cotton fabric.

3. The combination of a female condom device and an insertion device, said condom device comprising a triangular pubic area cover pad having a front side and a back side, a thin elastomeric tubular condom portion affixed to said pad with the opening of said condom portion generally in the center of said front side and the closed end of said condom extending outwardly from said back side, and two hip engaging elongated loops of tape extending outwardly from the three corners of said pad; said insertion device comprising an elongated cylindrical bullet-shaped instrument having on its cylindrical surface a plurality of parallel longitudinal ribs and being adapted to be inserted into said condom portion and to position and condom portion inside the vagina of the wearer.

* * * * *